United States Patent
Wagner

(10) Patent No.: US 6,526,993 B1
(45) Date of Patent: Mar. 4, 2003

(54) DENTAL IMPLEMENT WITH COMFIT GRIP

(76) Inventor: Eugene C. Wagner, 1626 Chastain Pkwy. East, Pacific Palisades, CA (US) 90272

(*) Notice: Subject to any disclaimer, the term of this patent is extended or adjusted under 35 U.S.C. 154(b) by 64 days.

(21) Appl. No.: 09/660,387

(22) Filed: Sep. 12, 2000

(51) Int. Cl.$^7$ ............................................... A61C 15/02
(52) U.S. Cl. ................ 132/321; 132/200; 15/104.94; 426/134; 424/401
(58) Field of Search .................. 132/321, 200, 132/322, 323, 328, 329, 308, 309, 311; 401/52, 195; 433/140, 215; 15/104.93, 104.94; 426/132, 134, 104; 424/49, 52, 401; 604/77; 600/240

(56) References Cited

U.S. PATENT DOCUMENTS

| | | | |
|---|---|---|---|
| 106,773 A | * 8/1870 | Blake | 132/322 |
| 1,527,845 A | 2/1925 | Daniel | |
| D74,119 S | * 12/1927 | Nelson | D1/102 |
| 2,857,908 A | 10/1958 | Cornfield | |
| 3,078,856 A | 2/1963 | Bender | |
| 3,101,727 A | * 8/1963 | Wiseman | 132/329 |
| 4,229,482 A | * 10/1980 | Kreske, Jr. | 426/134 |
| 4,237,911 A | 12/1980 | White | |
| 4,238,510 A | * 12/1980 | Cherukuri et al. | 426/5 |
| 4,522,595 A | * 6/1985 | Selvidge | 433/142 |
| 4,610,871 A | * 9/1986 | Lynch | 424/48 |
| 5,016,659 A | 5/1991 | Mas | |
| D320,300 S | * 10/1991 | Good et al. | D1/104 |
| 5,085,634 A | 2/1992 | Lackney | |
| 5,113,880 A | * 5/1992 | Honda et al. | 132/321 |
| 5,253,661 A | * 10/1993 | Alonzo | 132/321 |
| 5,288,497 A | * 2/1994 | Stanley et al. | 424/440 |
| 5,293,886 A | 3/1994 | Czapor | |
| 5,337,766 A | 8/1994 | Lane | |
| 5,833,954 A | * 11/1998 | Chow et al. | 424/49 |
| 5,875,798 A | * 3/1999 | Petrus | 132/321 |
| 5,924,430 A | * 7/1999 | Baldauf | 132/321 |
| 5,980,456 A | * 11/1999 | Falcone | 600/240 |

\* cited by examiner

*Primary Examiner*—Kevin Shaver
*Assistant Examiner*—David C. Comstock
(74) *Attorney, Agent, or Firm*—Seth Natter; Natter & Natter

(57) ABSTRACT

A dental implement includes an elongate body having a dental tool at one or both ends and a comfit grip which is attached to the body and employed for manipulating the tools. The comfit grip includes an oral hygiene enhancement constituent carried in an electuary. The comfit grip may be removed from the implement body and placed in the user's oral cavity for release of the oral hygiene enhancement constituent through contact with saliva and/or by chewing. The oral hygiene enhancement constituent may comprise an anticaries agent, a malodor inhibitor, a tooth whitener, a plaque inhibitor or other constituents known to have oral hygiene enhancement properties.

20 Claims, 2 Drawing Sheets

DENTAL IMPLEMENT WITH COMFIT GRIP

BACKGROUND OF THE INVENTION

1. Field of the Invention

This invention relates generally to oral hygiene appliances and more particularly to a consumer dental appliance combined with a mechanism for release of an oral hygiene enhancement ingredient.

2. Antecedents of the Invention

For many years, toothpicks have been routinely used for removal of food particles lodged between teeth. It has also been known to impregnate wood toothpicks with mint flavoring. Employment of toothpicks, however, has been relegated to situations where more effective and complete oral hygiene practices cannot be achieved, e.g. after meals away from home wherein a toothbrush and dental floss were not readily available or the use of which would be impractical.

The inherent advantages of the toothpicks were that they provided a relatively easy "fix" to an immediate problem on hand, i.e. the dislodgement of food particles, and could be easily carried on one's person or were readily available at a dining facility.

There was a need, however, for enhanced oral hygiene practices in situations where more complete oral hygiene techniques, e.g. brushing, flossing, rinsing, etc. were not practical.

U.S. Pat. No. 4,237,911 disclosed an oral hygiene product having a wedge shaped fin and a stem formed of cellular material covered by a protective skin. The fin was employed to cleanse by being drawn through the spaces between teeth. Thereafter, the stem was to have been cut or broken and folded to expose the cellular material which was then rubbed over tooth surfaces for cleansing and/or chewed. The cellular material included oral hygiene products such as plaque inhibitors, plaque stain, fluoride, etc.

It is unknown whether the device disclosed in U.S. Pat. No. 4,237,911 was commercialized. It is evident, however, that if it was sold, it did not gain commercial acceptance, perhaps because the use thereof was difficult or the costs involved in manufacture prohibited commercial exploitation. Further, the use of the product would not be obvious to a casual purchaser observing a point of sale display, for example, and it would also appear that one would be reluctant to take out such device for use in public view.

SUMMARY OF THE INVENTION

A dental implement includes a dental tool at one end of an elongate body. Typical dental tools include scalers, curved picks, interdental stimulators, interproximal brushes, floss holders, etc. A similar or different tool is provided at the other end of the body.

The body includes a comfit grip formed of an electuary, e.g. a sugarless confection, a soft lozenge, chewing gum, a hard candy, etc. An active ingredient of the comfit grip serves an oral hygiene enhancement function and may include an anticaries agent, an antibacterial agent, a plaque inhibitor, a malodor inhibitor, a fluoride compound, etc. The oral hygiene enhancement ingredient is released into the oral cavity when the comfit grip is dissolved or chewed, etc. and is carried by and administered in the oral cavity by saliva.

The comfit grip may be stripped from the body and placed in the oral cavity after or before the dental tool(s) have been employed employed in a conventional manner. Alternately, the comfit grip is placed in the oral cavity for release of the active ingredient together with a portion of the implement body and only the implement is removed.

The implement body itself may be formed of a dissolvable electuary and provided with a releasable active ingredient.

From the foregoing compendium, it should be appreciated that an aspect of the present invention is to provide a dental implement with comfit grip of the general character described which is not subject to the disadvantages of the antecedents aforementioned.

It is a feature of the present invention to provide a dental implement with comfit grip of the general character described which promotes multiple oral hygiene techniques.

A consideration of the present invention is to provide a dental implement with a comfit of the general character described which may be inconspicuously employed in social situations.

Another feature of the present invention is to provide a dental implement with a comfit of the general character described which is relatively low in cost.

A further aspect of the present invention is to provide a dental implement with a comfit of the general character described which is well adapted for low cost mass production fabrication.

Another consideration of the present invention is to provide a dental implement with a comfit grip of the general character described which promotes effective oral hygiene in situations wherein conventional toothbrushing and mouth rinsing are impractical.

A still further aspect of the present invention is to provide a dental implement with a comfit grip of the general character described a portion of which is dissolvable within the oral cavity to release an oral hygiene enhancement constituent.

Yet another feature of the present invention is to provide a dental implement with a comfit of the general character described wherein the comfit is formed of a chewing gum confection which releases an oral hygiene enhancement constituent.

Yet another aspect of the present invention is to provide a dental implement with a comfit grip of the general character described which is useful for both the dislodgement of food particles and for dispensing an oral hygiene enhancement ingredient.

To provide a dental implement with a comfit grip of the general character described wherein the grip includes an oral hygiene enhancement ingredient released when the comfit is dissolved by saliva is a still further consideration of the present invention.

Yet another feature of the present invention is to provide a dental implement with a comfit grip of the general character described wherein the grip is formed of an elecutory which releases an oral hygiene promoting agent when dissolved in the oral cavity.

To provide a dental implement of the general character described including a dental tool at least a portion of which is formed of a confection which releases an oral hygiene constituent is yet another feature of the present invention.

Other aspects, features and considerations of the present invention in part will be obvious and in part will be pointed out hereinafter.

With these ends in view, the invention finds embodiment in the various combinations of elements, arrangements of parts and series of steps by which the aforesaid aspects, features and considerations and certain other aspects, features and considerations are attained, or with reference to the accompanying drawings in the scope of which will be more particularly pointed out and indicated in the appended claims.

BRIEF DESCRIPTION OF THE DRAWINGS

In the accompanying drawings in which are shown some of the various possible exemplary embodiments of the invention.

DESCRIPTION OF THE PREFERRED EMBODIMENT

Figure 1:
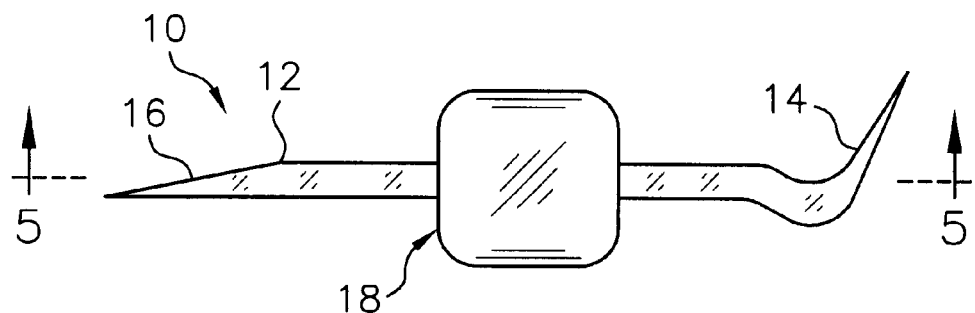
FIG. 1 is a top plan view of a dental implement constructed in accordance with and embodying the present invention with the implement comprising an elongate body having a dental tool at each end and a comfit grip affixed to the body between the ends.
Figure 2:
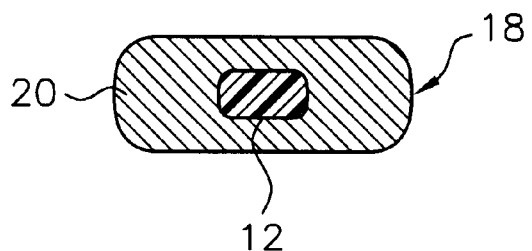
FIG. 2 is a transverse sectional view through the implement, the same being taken substantially along the line 2—2 of FIG. 1 and through the comfit grip and the body and showing the comfit grip formed of a single piece of hard confection.

Referring now in detail to the drawings, the reference numeral 10 denotes generally a dental implement constructed in accordance with and embodying the invention. The dental implement 10 includes an elongate body 12 formed of a suitable polymer. At one end of the body 12 there is provided a dental tool 14 comprising a curved pick while the other end of the body is formed with a wedge shaped pick 16. In accordance with the invention, affixed to the body 12 between the tools 14, 16 there is a grip 18 formed of an electuary comfit.

The comfit grip 18 may comprise a hard, sugarless, artificially sweetened comfit such as a confection or lozenge 20 having an ingredient for oral hygiene enhancement such as an anticaries agent, a plaque inhibitor, a tooth whitener, and/or a breath freshener. Specific ingredients may include, for example, sodium bicarbonate, calcium carbonate, calcium peroxide, and fluoride compounds. Further, breath freshening and/or malodor inhibitors are provided such as menthol, eucalyptus oil, chlorophyll, thymol, chlorine dioxide and zinc chloride.

In accordance with the invention, the dental tools 14, 16 are employed in the usual manner with the body of the implement being grasped at the comfit grip 18 between one's fingers, preferably the index finger and the thumb for efficacious manipulation of the tools.

Figure 6:
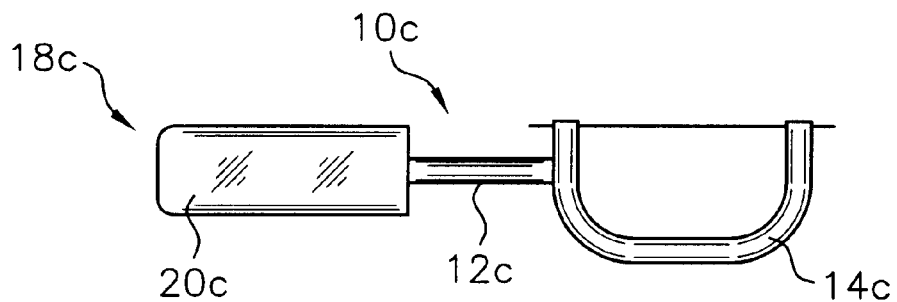
FIG. 6 is a top plan view of an alternate dental implement having a dental tool comprising a floss applicator at one end of a body and a comfit grip at the other end.
Figure 7:
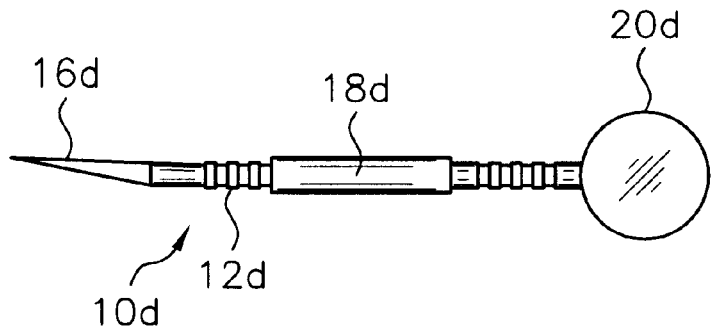
FIG. 7 is a top plan view of a further alternate dental implement which includes a dental tool comprising a wedge pick at one end of a body, a comfit at the other end and a grip at the center.

As will be observed from an examination of the drawing figures, the comfit grip 18 includes a pair of broad faces which are generally parallel to one another. The faces have a width in the order of three times the width of the elongate body 12, as shown in FIGS. 1–4 and a length in the order of at least three times the width of the elongate body 12, as shown in FIG. 1, FIG. 6 and FIG. 7. Additionally, the thickness of the comfit grip 18, i.e. the distance between the faces, is in the order of three times the thickness of the elongate body 18, as shown in FIGS. 2–5.

In plan view, the faces may be shaped in various geometric configurations suitable for being grasped, e.g. square (FIG. 1), rectangular (FIG. 6) or circular (FIG. 7).

After the dental tools have been employed in the customary manner to dislodge food particles, massage gingival surfaces, scraping, etc., the comfit grip 18 may be stripped from the body by being pulled in an axial direction toward the tool 16 and then deposited within the user's mouth. Alternately, the implement 10, together with the comfit grip 18, may be placed in the user's mouth.

The saliva in the user's mouth dissolves the electuary confection 20, resulting in the release of the oral hygiene enhancement constituent(s) within the user's oral cavity carried by the saliva for effective distribution, thus attaining the inherent therapeutic advantages thereof. If the dental implement 10 and comfit have been placed in the oral cavity together, after the comfit has dissolved or is stripped from the body, the implement is removed and may be discarded or reused, as desired.

Figure 3:
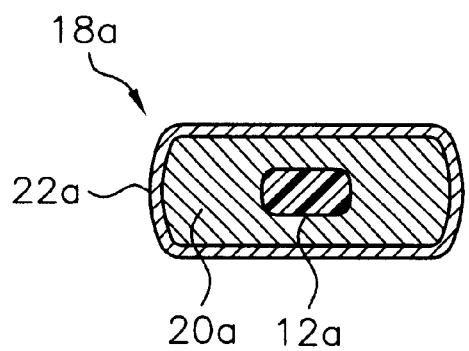
FIG. 3 is a transverse sectional view through the dental implement and comfit grip, similar to that of FIG. 2, however through an alternate comfit grip comprising chewing gum formed with a hard outer covering.

In FIG. 3 an alternate comfit grip 18a is disclosed. The grip 18a comprises a chewing gum core 20a surrounded by a hard coating 22a. The comfit grip 18a may be stripped from the body of its implement and placed in the oral cavity after the tool or tools of the implement have been used in a conventional manner. Alternately, the implement together with the comfit grip 18a are placed in the oral cavity with the hard coating 20a being dissolved and/or broken by chewing action. Thereafter the comfit grip 18a is stripped from the body and the body is removed. The hard coating 22a and/or chewing gum 20a are impregnated with oral hygiene enhancement constituents which are released upon chewing.

Figure 4:
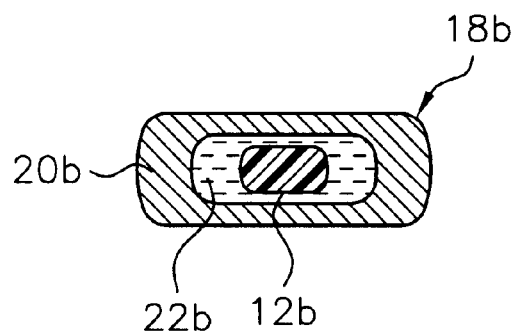
FIG. 4 is a transverse sectional view through the dental implement and comfit grip, similar to that of FIG. 2, however through an alternate comfit grip formed of a hard confection with a liquid center.
Figure 5:
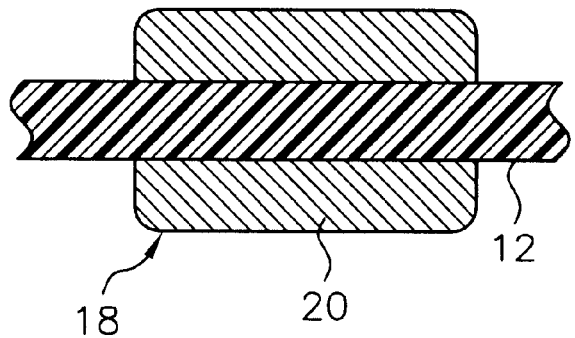
FIG. 5 is an enlarged scale fragmentary longitudinal sectional view through the dental implement, the same being taken substantially along the line 5—5 of FIG. 1.

In FIG. 4 there is illustrated a further configuration of a comfit grip 18b, comprising a hard confection 20b having an internal liquid center 22b, with the liquid center 22b carrying the oral hygiene enhancement ingredients. Optionally, the oral hygiene enhancement ingredients will be carried in the hard confection 20b, or both.

With reference now to FIG. 6, there is shown an alternate implement 10c comprising a body 12c with a dental tool 14c at one end thereof. The dental tool 14c is configured as a dental floss holder and applicator. Pursuant to the invention, a comfit grip 18c is attached to the body 12c at the opposite end thereof.

Illustrated in FIG. 7 is a further dental implement 10d including a body 12d having a pick 14d at one end thereof and a comfit 20d carrying an oral hygiene enhancement constituent at the other end thereof. Intermediate the ends of the body 12d is a grip portion 18d which need not comprise a comfit. The grip portion 18d is used to manipulate the pick 14d.

Figure 8:
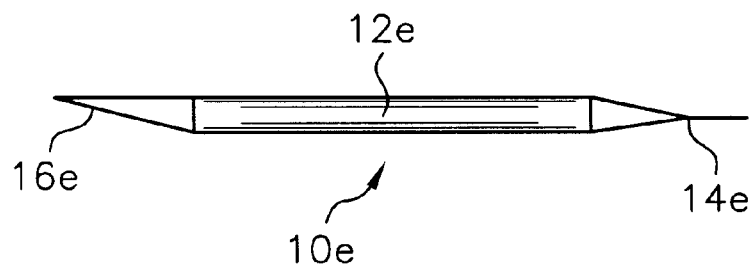
FIG. 8 is a top plan view of a further embodiment of the invention wherein the implement body is formed of a hard confection, with the body being dissolvable in the oral cavity to release a dental hygiene enhancement ingredient.

A still further embodiment of the invention is depicted in FIG. 8. In this embodiment, an elongate body 12e has formed at one end thereof, a conventional pick 14e and at the other end thereof a wedge pick 16e.

Pursuant to the invention, the length of the body 12e serves as a comfit grip and the entire body 12e is therefore formed of a hard confection having oral hygiene enhancement constituent ingredients which are released by being dissolved in saliva when the body 12e is placed within the oral cavity.

It should be noted that the specific dental tools provided at one or both ends of the body of the implement are of conventional configuration and the placement of the comfit is a function of providing ease of usage. Thus, the comfit need not be positioned along the body at the center thereof, i.e. between the ends of the body. It may be positioned anywhere along the length of the body. If employed as a grip, the comfit is positioned such that grasping the implement at the comfit will facilitate manipulation of the tool.

It should also be noted that with the exception of the FIG. 8 embodiment, the implement body and dental tools need not be fabricated solely of a polymer material. Wood, or metal may be employed or a combination of a polymer body and rubber or metal tipped tools may also be utilized. Metal has been found particularly advantageous as a pick, scaler or scraping tool while rubber tipped tools such as stimulators and polishers are also useful.

Thus it will be seen that there is provided a dental implement with comfit grip which achieves the various aspects, features and considerations of the present invention and which is well adopted to meet the conditions of practical usage.

Since various possible embodiments might be made of the present invention and since various changes might be made in the exemplary embodiments shown herein without departing from the spirit of the invention, it should be understood that all matter herein described or shown in the accompany drawings should be interpreted as illustrative and not in a limiting sense.

Having thus described the invention, there is claimed new and desired to be secured by Letters Patent:

1. A dental implement for enhanced oral hygiene practices, the implement comprising an elongate body, the body having a length, a width and a thickness, the body including a dental tool at one end thereof and a comfit grip attached to the body, the comfit grip being graspable between a user's thumb and forefinger for manipulating the dental tool in the user's oral cavity, the comfit grip including a pair of broad faces spaced apart a distance greater than the thickness of the body and having a width at least three times the width of the body, the comfit grip carrying an oral hygiene enhancement constituent, the constituent being dispensed into the oral cavity of the user through contact with saliva.

2. A dental implement for enhanced oral hygiene practices as constructed in accordance with claim 1 wherein the comfit grip comprises a confection.

3. A dental implement for enhanced oral hygiene practices as constructed in accordance with claim 2 wherein the confection is artificially sweetened.

4. A dental implement for enhanced oral hygiene practices as constructed in accordance with claim 2 wherein the confection comprises chewing gum.

5. A dental implement for enhanced oral hygiene practices as constructed in accordance with claim 2 wherein the confection comprises a hard candy having a liquid center, the oral hygiene enhancement constituent being carried in the liquid center.

6. A dental implement for enhanced oral hygiene practices as constructed in accordance with claim 1 wherein the oral hygiene enhancement constituent comprises an anticaries agent.

7. A dental implement for enhanced oral hygiene practices as constructed in accordance with claim 1 wherein the oral hygiene enhancement constituent comprises a fluoride compound.

8. A dental implement for enhanced oral hygiene practices as constructed in accordance with claim 1 wherein the oral hygiene enhancement constituent comprises a malodor inhibitor.

9. A dental implement for enhanced oral hygiene practices as constructed in accordance with claim 1 wherein the oral hygiene enhancement constituent comprises a tooth whitener.

10. A dental implement for enhanced oral hygiene practices as constructed in accordance with claim 1 wherein the comfit grip is positioned at the other end of the body.

11. A dental implement for enhanced oral hygiene practices as constructed in accordance with claim 1 wherein the comfit grip is positioned at the midlength of the body.

12. A dental implement for enhanced oral hygiene practices as constructed in accordance with claim 1 wherein the oral hygiene enhancement constituent is selected from the group consisting of sodium bicarbonate, calcium carbonate, calcium peroxide, a fluoride compound, menthol, eucalyptus oil, chlorophyll, thymol and zinc chloride.

13. A dental implement for enhanced oral hygiene practices as constructed in accordance with claim 1 wherein the dental implement includes a second dental tool, the second dental tool being positioned at the other end of the body.

14. A dental implement for enhanced oral hygiene practices as constructed in accordance with claim 1 wherein the oral hygiene enhancement constituent comprises a breath freshener.

15. A dental implement for enhanced oral hygiene practices as constructed in accordance with claim 1 wherein the faces are substantially square in plan configuration.

16. A dental implement for enhanced oral hygiene practices as constructed in accordance with claim 1 wherein the faces are substantially circular in plan configuration.

17. A dental implement for enhanced oral hygiene practices as constructed in accordance with claim 1 wherein the faces are substantially rectangular in plan configuration.

18. A dental implement for enhanced oral hygiene practices as constructed in accordance with claim 1 wherein the oral hygiene enhancement constituent comprises a coating.

19. A method of practicing oral hygiene with the dental implement constructed in accordance with claim 1, the method comprising the steps of:
   a) grasping the dental implement by the comfit grip,
   b) manipulating the tool in the fashion customary for conventional usage thereof while holding the comfit grip between the user's thumb and forefinger,
   c) separating the comfit grip from the body,
   d) placing the comfit grip in the user's oral cavity, and
   e) dispensing the oral hygiene enhancement constituent in the user's oral cavity with saliva.

20. A method of practicing oral hygiene with the dental implement constructed in accordance with claim 1, the method comprising the steps of:

a) grasping the dental implement by the comfit grip,
b) manipulating the tool in the fashion customary for conventional usage thereof while holding the comfit grip between the user's thumb and forefinger,
c) placing the comfit grip in the user's oral cavity,
d) separating the comfit grip from the body, and
e) dispensing the oral hygiene enhancement constituent in the oral cavity with saliva.

* * * * *